United States Patent
Papathanassiu (12) 
(10) Patent No.: US 6,528,489 B1
(45) Date of Patent: Mar. 4, 2003

(54) MYCOTOXIN DERIVATIVES AS ANTIMITOTIC AGENTS

(75) Inventor: Adonia E. Papathanassiu, Silver Spring, MD (US)

(73) Assignee: Ergon Pharmaceuticals LLC, Washington, DC (US)

( * ) Notice: Subject to any disclaimer, the term of this patent is extended or adjusted under 35 U.S.C. 154(b) by 0 days.

(21) Appl. No.: 09/667,036

(22) Filed: Sep. 21, 2000

Related U.S. Application Data (60) Provisional application No. 60/155,625, filed on Sep. 23, 1999.
(51) Int. Cl.[7] .................. A61K 31/122; A61K 31/335; A61K 38/05; A61K 38/07; A61K 38/10
(52) U.S. Cl. .............. 514/14; 514/18; 514/19; 514/450; 514/456; 514/460; 514/680; 530/326; 530/330; 544/282; 549/270; 549/292; 568/326
(58) Field of Search .................. 514/14, 15, 450, 514/456, 460, 680, 18, 19; 530/326, 327, 330; 544/282; 549/270, 292; 568/326

(56) References Cited

U.S. PATENT DOCUMENTS 4,842,862 A * 6/1989 Jacobs et al. ............... 424/422
5,003,056 A * 3/1991 Nishikiori et al. .......... 536/7.1

FOREIGN PATENT DOCUMENTS

JP  4-26631  * 1/1992

* cited by examiner

Primary Examiner—Jeffrey E. Russel

(57) ABSTRACT

The present invention provides a treatment for mammalian diseases characterized by aberrant cell proliferation. The treatment consists of administering therapeutically active dosages of antibiotic inhibitors such as efrapeptin oligopeptides or mycotoxin derivatives including those comprising a-zearalenol structural motifs resulting in inhibition of cell mitosis.

5 Claims, 9 Drawing Sheets

Aurovertin b

Citreoviridin

α-Zearalenol

Oligomycin A

FIG. 1A

Oligomycin B

FIG. 1B

Oligomycin C

FIG. 1C

Aurovertin b

Citreoviridin

α-Zearalenol

FIG. 2

Efrapeptin A:

Ac-AIB-GLY-LEU-isoVAL-X

Efrapeptin B:

Ac-LEU-isoVAL-X

Efrapeptin C (SEQ ID No: 1)

Ac-PIP-AIB-PIP-AIB-AIB-LEU-β-ALA-GLY-AIB-AIB-PIP-AIB-GLY-LEU-AIB-X

Efrapeptin D (SEQ ID No: 2)

Ac-PIP-AIB-PIP-AIB-AIB-LEU-β-ALA-GLY-AIB-AIB-PIP-AIB-GLY-LEU-isoVAL-X

Efrapeptin E (SEQ ID No: 3)

Ac-PIP-AIB-PIP-isoVAL-AIB-LEU-β-ALA-GLY-AIB-AIB-PIP-AIB-GLY-LEU-isoVAL-X

Efrapeptin F (SEQ ID No: 4)

Ac-PIP-AIB-PIP-AIB-AIB-LEU-β-ALA-GLY-AIB-AIB-PIP-AIB-ALA-LEU-isoVAL-X

Efrapeptin G (SEQ ID No: 5)

Ac-PIP-AIB-PIP-isoVAL-AIB-LEU-β-ALA-GLY-AIB-AIB-PIP-AIB-ALA-LEU-isoVAL-X where
Ac = acetyl,
AIB = α-amino-isobutyric acid,
PIP = pipecolic acid, and

MYCOTOXIN DERIVATIVES AS ANTIMITOTIC AGENTS

The present nonprovisional patent application claims benefits of provisional patent application entitled "Mycotoxin derivatives as antimitotic agents" with filing date Sep. 23, 1999 and patent application Ser. No. 60/155,625.

FIELD OF THE INVENTION

The present invention relates to the compositions and methods for the inhibition of cellular proliferation. More particularly, the present invention relates to the use of antibiotics such as efrapeptins, oligomycins, mycotoxins, or mycotoxin derivatives including those comprising aurovertin B, citreoviridin, and α-zearalenol structural motifs for the treatment of hyperproliferative diseases such as cancer, atherosclerosis, and psoriasis.

BACKGROUND OF THE INVENTION

Cell growth is a normal process that is vital to the well-being of all living organisms. It involves two major events: the duplication of DNA and the physical division of the cell into two daughter cells (Rew, D. A., et al. Cell production rates in human tissues and tumours and their significance, *Eur. J. Surg. Oncol.*, 26(4), 405–17 (2000)). Under physiological conditions, cell proliferation is highly regulated; in any given tissue, the fraction of dividing cells depends on the age of the organism and the properties of the tissue. For example, embryos and young animals contain a large fraction of proliferating cells. On the other hand, in adults, sustained cell growth is observed only in specific tissues, such as the intestine. The majority of adult mammalian cells are in a quiescent state.

Whether an adult mammalian cell will grow and divide or become quiescent is determined by a variety of extrinsic and intrinsic regulatory mechanisms such as the availability of space, the presence of growth-stimulatory or growth-inhibitory signals in the immediate cell environment, or the number of previous cell divisions (Fortunel, N., et al. High proliferative potential-quiescent cells: a working model to study primitive quiescent hematopoietic cells. *J Cell Sci.*, 111,1867–75 (1998)). Disruption of these mechanisms leads to an abnormal cellular proliferation and the development of pathological conditions known as hyperproliferative diseases (Skobe, M, et al., Tumorigenic conversion of immortal human keratinocytes through stromal cell activation, *Proc. Nati. Acad. Sci. USA*, 95(3), 1050–5 (1998)). As used herein, the term "hyperproliferative diseases" refers to pathological situations characterized by aberrant cellular growth. Cancer is an example of a hyperproliferative disease. Cancer is the result of an uncontrolled cell growth due to genetic alterations that allow cells to divide indefinitely (Studzinski, G. P., et al. Oncogenes, growth, and the cell cycle: an overview. *Cell Tissue* Kinet. 22(6), 405–24 (1989)). On the other hand, neovascularization is the result of an abnormal endothelial cell proliferation due to the presence of excess of growth-stimulatory signals in the endothelial cell environment.

Angiogenesis or neovascularization is the formation of new blood vessels from pre-existing capillaries via a mechanism that involves degradation of the basement membrane that surrounds the parent vessel, migration of endothelial cells through the degraded membrane, proliferation of the migrating cells, endothelial cell differentiation, and loop formation (Folkman, J., Angiogenesis and angiogenesis inhibition: an overview, *EXS.*, 79, 1–8 (1997)). With the exception of wound healing and menstruation, angiogenesis in adults is observed only in pathological situations such as cancer, atherosclerosis, and psoriasis, where it contributes to the progression and symptom manifestation of the disease (Folkman, J. Angiogenesis in cancer, vascular, rheumatoid and other disease, *Nat. Med.* 1(1), 27–31 (1995)). Other "angiogenesis-related" diseases include endometriosis, Kaposi's sarcoma and other HIV-related conditions, leukemia, scleroderma, pyogenic granuloma, myocardial angiogenesis, corneal diseases, rubeosis, neovascular glaucoma, diabetic retinopathy, macular degeneration, and retrolental fibroplasia. As used herein, the term "angiogenesis-related diseases" means pathological conditions that require endothelial cell proliferation for progression and symptom manifestation (Chappey, O., et al. Endothelial cells in culture: an experimental model for the study of vascular dysfunctions. *Cell Biol. Toxicol.*, 12(4–6), 199–205 (1996)).

Increasing experimental evidence suggest that angiogenesis plays an essential role in cancer development. It has been observed that solid tumors neither grow beyond 1–2 $mm^3$ nor metastasize unless they become vascularized (Folkman, J. What is the Evidence that Tumors are Angiogenesis Dependent?, *J Natl. Canc. Inst.*, 82, 4–6 (1990)). Formation of tumor vasculature is necessary in order to deliver nutrients and oxygen at the tumor site, thus providing a route for tumor metastasis to distant sites. Compounds that inhibit endothelial cell proliferation have been shown to inhibit tumor neovascularization, and to prevent tumor growth and metastasis (Eatock, M. M., et al. Tumour vasculature as a target for anticancer therapy. *Cancer Treat Rev.* 26(3), 191–204 (2000)). Several of these inhibitors are currently under evaluation in human clinical trials (Deplanque, G., et al. Anti-angiogenic agents: clinical trial design and therapies in development, *Eur. J Cancer*, 36, 1713–1724 (2000)).

It is clear that therapies directed to control cellular growth, particularly endothelial cell proliferation, and most particularly angiogenesis, can have a therapeutic impact in hyperproliferative diseases, particularly those referred to as angiogenesis-related conditions. Therefore, what is needed is a composition and method, which inhibits undesirable cellular proliferation, especially the growth of blood vessels into tumors. The composition should preferably be non-toxic and produce few side effects.

SUMMARY OF THE INVENTION

In accordance with the present invention, compositions and methods are provided which are effective in inhibiting undesirable cell growth including, but not limited to, abnormal endothelial cell proliferation and tumor cell growth. The composition provided herein contains an antibiotic molecule such as efrapeptins, oligomycins, mycotoxins such as aurovertin B, citreoviridin, and α-zearalenol or a mycotoxin derivative described in the general formula found below. Efrapeptins are a family of apolar, hydrophobic peptides isolated from entomopathogenic fungi. With the exception of efrapeptin A and B, efrapeptins are composed of 15 amino acids (usually common amino-acids alanine, glycine, leucine and uncommon amino-acids α-aminobutyric acid, β-alanine, isovaline, and pipecolic acid) with the amino-terminal acetylated and the carboxyl-terminal blocked by N-peptido-1-isobutyl-2[1-pyrrole-(1,2-α)-pyrimidinium,2,3,4,5,6,7,8,-hexahydro]-ethylamine (Krasnoff, S. B., et al., Antifungal and Insecticidal Properties of the Efrapeptins: Metabolites of the Fungus *Tolypocladium niveum, J Invert. Path.*, 58, 180–188 (1991)). Mycotoxins are secondary metabolites produced by many pathological and food spoilage fungi including Aspergillus, and Penicillium species. For example, aurovertin B is produced by *Calcarisporium Arbuscula*, citreoviridin is produced by Penicillium Citreoviride Biourge, while α-zearalenol is produced by Fusarium (Mulheim, L. J. et al., *J Chem. Soc.*, Chem. Commun. 874 (1974), Franck, B., et al. Citreoviridins from *Aspergillus terreus, Angew Chem. Int. Ed. Engl.*, 19(6), 461–2 (1980), and Stipanovic, R. D., et al., Zearalenol and 8'-hydroxyzearalenone from *Fusarium roseum*, 57(2), 77–8 (1975)).

The methods provided herein for treating diseases mediated by endothelial cell proliferation involve administering to a human or animal a composition containing therapeutic dosages of efrapeptis, oligomycins, aurovertin B, citreoviridin, α-zearalenol, or a derivative thereof described in the general formula found below. The method is especially useful for treating angiogenesis-related diseases such as cancer, atherosclerosis, psoriasis, diabetic retinopathy, macular degeneration, endometriosis, Kaposi's sarcoma and other HIV-related disorders.

Accordingly, it is an object of the present invention to provide a method for treating diseases that are mediated by endothelial cell proliferation.

It is yet another object of the present invention to provide a composition for treating angiogenesis-related diseases in humans and animals.

BRIEF DESCRIPTION OF DRAWINGS

FIG. 4A and FIG. 4B are graphs depicting the ability of aurovertin B to inhibit bFGF-induced proliferation of endothelial cells. In FIG. 4A, proliferation of endothelial cells is reported as a cell number, while in FIG. 4B, proliferation of endothelial cells is reported as an absorbance.

COMPOUNDS ACCORDING TO THE INVENTION

As described below, compounds that are useful in accordance with the invention include efrapeptins, oligomycin A, B, C, and D, aurovertin B, citreoviridin, α-zearalenol, and novel mycotoxin derivatives. Specific novel compounds are described by the following formula:

where n=1–10

In the above formula $R_a$, $R_b$, $R_c$, and $R_d$ are independently selected from —H, —OH, =O, straight chained and branched alkanes, alkenes, alkynes; cyclic alkanes, alkenes, and alkynes; combinations of cyclic and acyclic alkanes, alkenes, and alkynes; alcohol, aldehyde, ketone, carboxylic acid, ester, or ether moieties; aza; amino; —$XO_n$ or —O—$OXO_n$ (where X=N and n=2; X=S and n=2 or 3; X=P and n=1–3) and halogens (—F, —Cl, —Br, —I). $Z_1$, and $Z_2$ can be selected from: —O, —$NR_1$, —$SR_1$, —$CR_1$, where $R_1$ is selected from —H, —OH, =O, straight chained and branched alkanes, alkenes, alkynes; cyclic alkanes, alkenes, and alkynes; combinations of cyclic and acyclic alkanes, alkenes, and alkynes; alcohol, aldehyde, ketone, carboxylic adic, ester, or ether moieties; aza; amino; —$XO_n$ or —O—$OXO_n$ (where X=N and n=2; X=S and n=2 or 3; X=P and n=1–3) and halogens (—F, —Cl, —Br, —I).

DETAILED DESCRIPTION OF THE INVENTION

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The present invention provides compositions and methods for the treatment of hyperproliferative diseases. The treatment comprises the administration of a mycotoxin or a mycotoxin-derivative in sufficient amount to inhibit undesirable cell proliferation, particularly endothelial cell proliferation, and most particularly angiogenesis, and angiogenesis-related diseases.

Antiproliferative Activity

Antiproliferative activity is evaluated by testing the ability of an antibiotic to inhibit endothelial and/or tumor cell growth in vitro. A proliferation assay typically involves the routine culturing of the endothelial or tumor cells to confluency in the appropriate media. Subsequently, the cells are trypsinized and plated in a 96-well plate at 2,500–10,000 cells per well. The cells are cultured for 96 hours in the present of the antimitotic agent and growth factors. Cell proliferation is determined using a spectrophotometry (MTT assay), fluorimetry (Cyquant assay), or cell counting.

Antiproliferative activity can be evaluated in situ by testing the ability of the antibiotic to inhibit formation of blood vessels in the chick embryo chorioallantoic membrane (CAM) described by Crum et al. (Crum et al., *Science*, 230, 1375 (1985)). Briefly, fertilized chick embryos are removed from their shell on day 3 or 4, and a methylcellulose disc containing the antiproliferative compound is implanted on the chorioallantoic membrane. The embryos are examined under the microscope 48 hours later. Presence of a clear avascular area around the methylcellulose disc is indicative of antiangiogenic activity. The larger the diameter of the zone is, the greater the antiangiogenic action is.

Indications

The invention can be used to treat any hyperproliferative diseases. Such diseases include, but are not limited to, cancer (solid tumor and leukemias), granulomas, abnormal wound healing, inflammatory and immune disorders, Bechet's disease, and angiogenesis accompanying atherosclerosis, rheumatoid arthritis, psoriasis, diabetic retinopathy, macular degeneration, endometriosis, Kaposis's sarcoma and other HIV-related disorders, corneal graft rejection, neuroscular glacoma and Oster Webber syndrome (Folkman, J., Angiogenesis in cancer, vascular, rheumatoid and other disease, Nat. Med., 1(1), 27–31 (1995)).

Administration

The compositions described previously may be administered by the topical, oral, rectal or parenteral (e.g., intravenous, subcutaneous or intramuscular) route. They may also be incorporated into biodegradable polymers for sustained release implanted at the disease site. The dosage of the compositions depends on the condition treated, the activity of the drug used, the route of administration, and other clinical factors such as the severity of the disease and the weight of the patient. The compositions are formulated in ways suitable for the specific route of administration. Formulations suitable for oral administration include capsules, cachets or tablets containing a predetermined amount of the active ingredient, powder or granules, solutions, suspensions, and emulsions. Formulations suitable for topical administration in the mouth include lozenges, pastilles, and mouthwashes. Formulations suitable for topical administration to the skin include ointments, creams, gels, pastes, and transdermal patches. Formulations for rectal administration may be presented as a suppository with a suitable base, while vaginal administrations maybe presented as pessaries, tampons, creams, gels, pastes, foams, and sprays comprising the active ingredient in an appropriate carrier. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

In addition, the compositions may administered in combination with other therapeutic interventions well known in those skilled in the art such as radiation, chemotherapy, and/or photodynamic treatment (PDT).

The invention is further understood by the following non-limiting examples, which are not to be construed in any way as imposing limitations upon the scope thereof On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Effect of Various Antibiotics on the basic Fibroblast Growth Factor (bFGF)-induced Proliferation of Human Endothelial Cells Proliferation assays familiar to those skilled in the art using human umbilical vein endothelial cells (HUVECs) were employed in order to determine the effect of various antibiotics on the growth of bFGF-stimulated HUVECs.

Materials and Methods

The materials for this experiments included endothelial cells (HUVECS) and media for their proliferation (Media 200, fetal bovine serum (FBS), gelatin, bFGF) (Paragon Bioservices, Baltimore, Md.), and Cell Titer 96 for detection of cell proliferation (Paragon Bioservices, Baltimore, Md.). Antibiotics aurovertin B, citreoviridin, oligomycin A, oligomycin B, oligomycin C, and efrapeptin D were all obtained from Sigma Chemical Company (St. Louis, Mo.).

HUVECs were routinely cultured to confluency in Media 200 containing 10% FBS. The cells were then trypsinized and plated in a 96-well plate pre-coated with 1% gelatin at 5000 cells per well per 100 µL Media 200 containing 2% FBS. The cells were allowed to adhere for 24 hours. Subsequently, the media were aspirated and fresh Media 200 containing 0.5% FBS were added to the wells. Addition of various concentrations of antibiotics in the presence and absence of 20 ng/ml bFGF followed. The assay plates were incubated at 37° C., 5% $CO_2$ for 48 hours. At the end of the incubation period, cell proliferation was determined using cell counting (Cell Counter Model Z1, Coulter Incorporation, Miami, Fla.) or spectrophotometry. In the later case, the assay plates were incubated with Cell Titer 96 for 2 hours and the absorbance was recorded at 490 nm.

Results

Figure 1A:
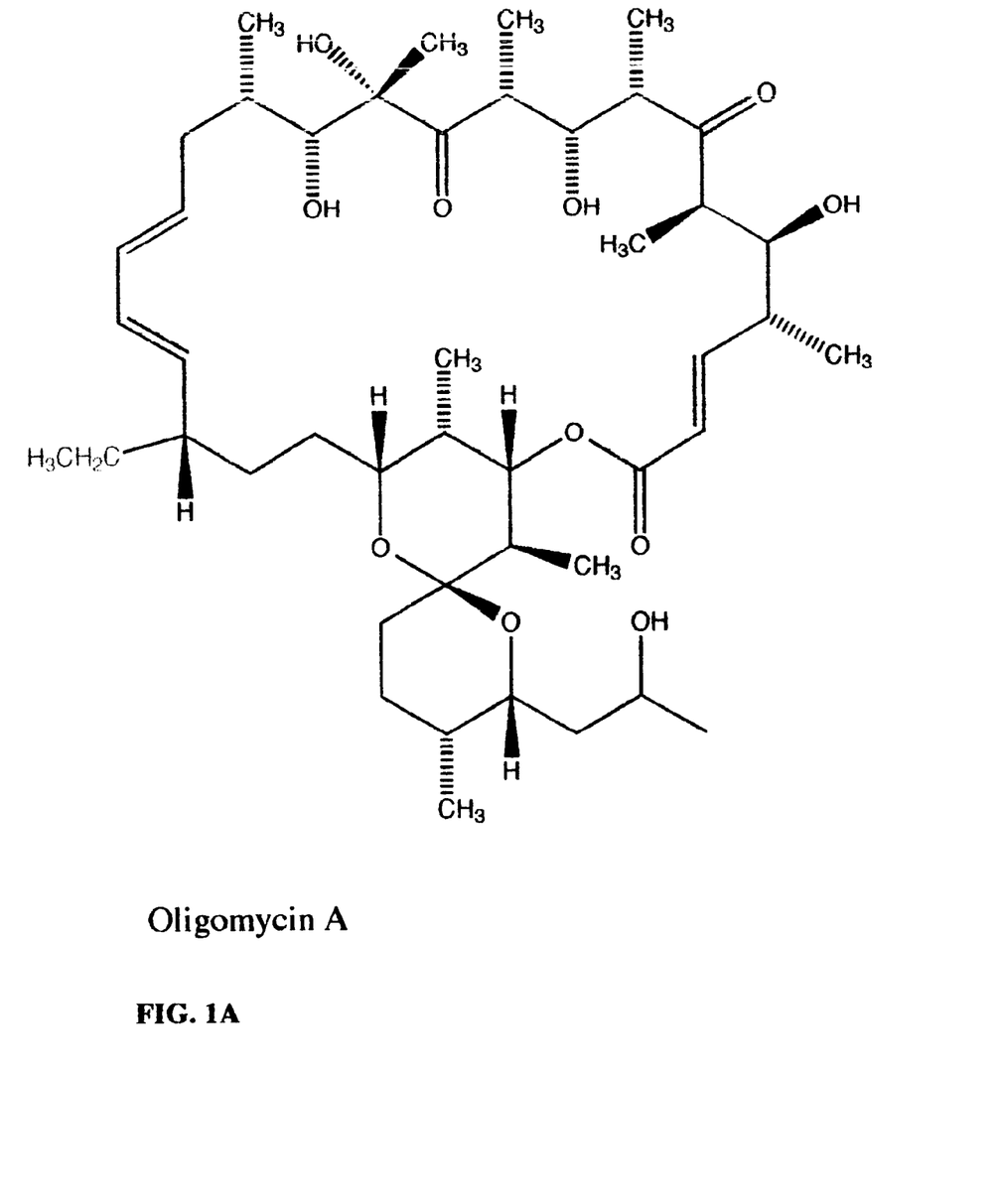
FIG. 1A is a schematic diagram showing the chemical structure of oligomycin A.
Figure 1B:
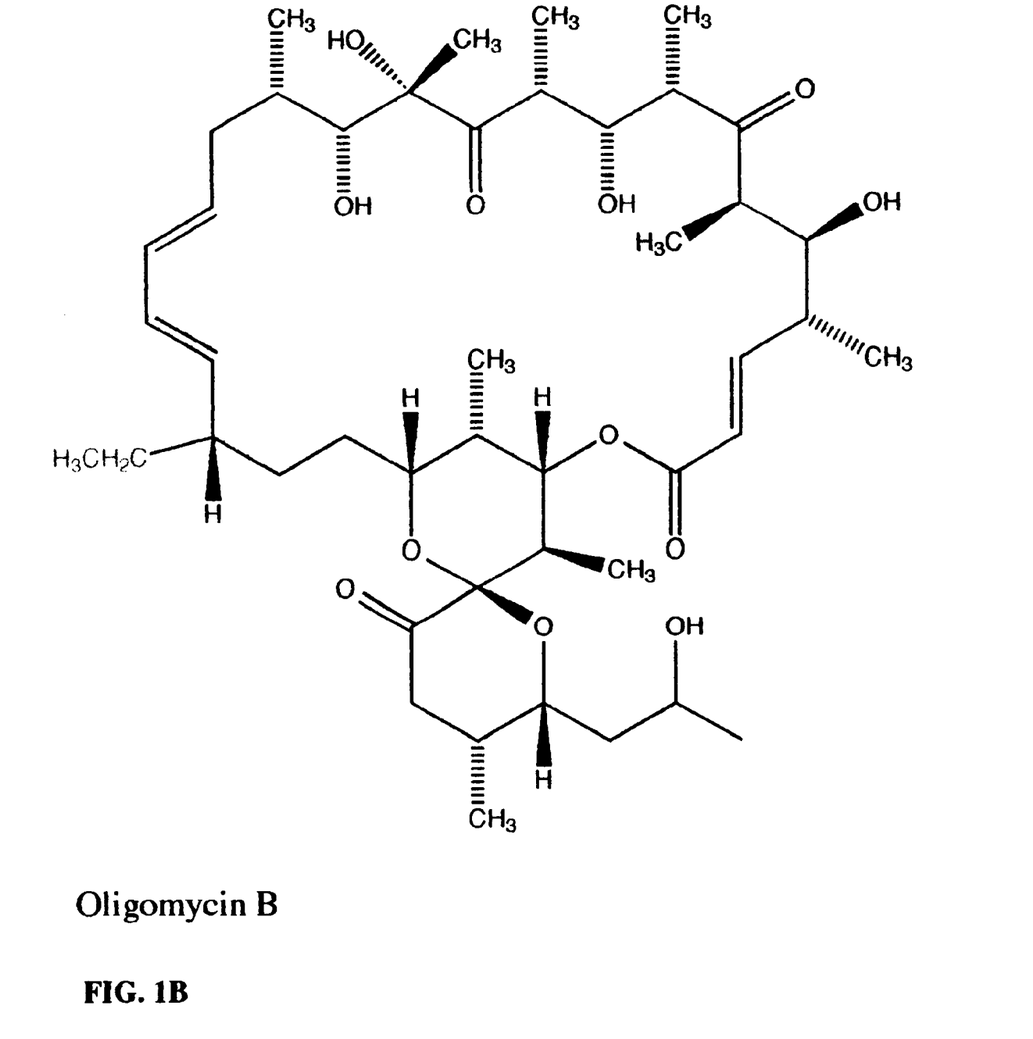
FIG. 1B is a schematic diagram showing the chemical structure of oligomycin B.
Figure 1C:
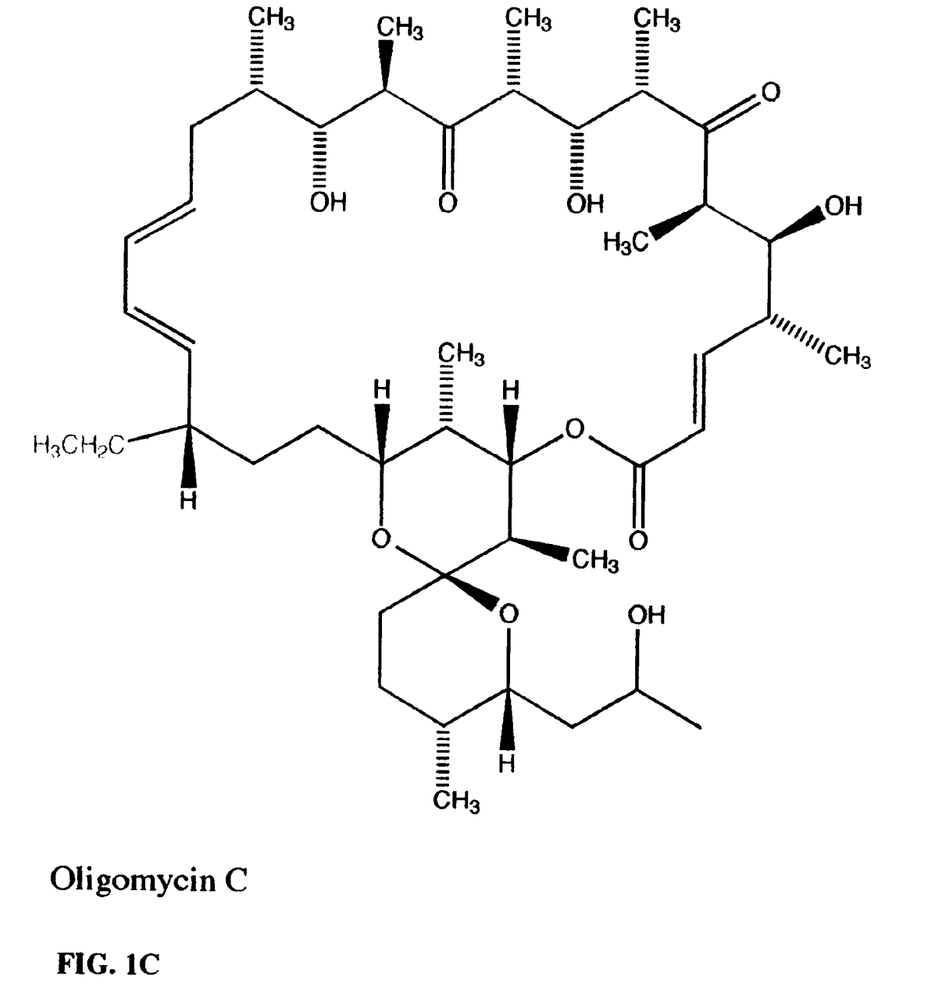
FIG. 1C is a schematic diagram showing the chemical structure of oligomycin C.
Figure 2:
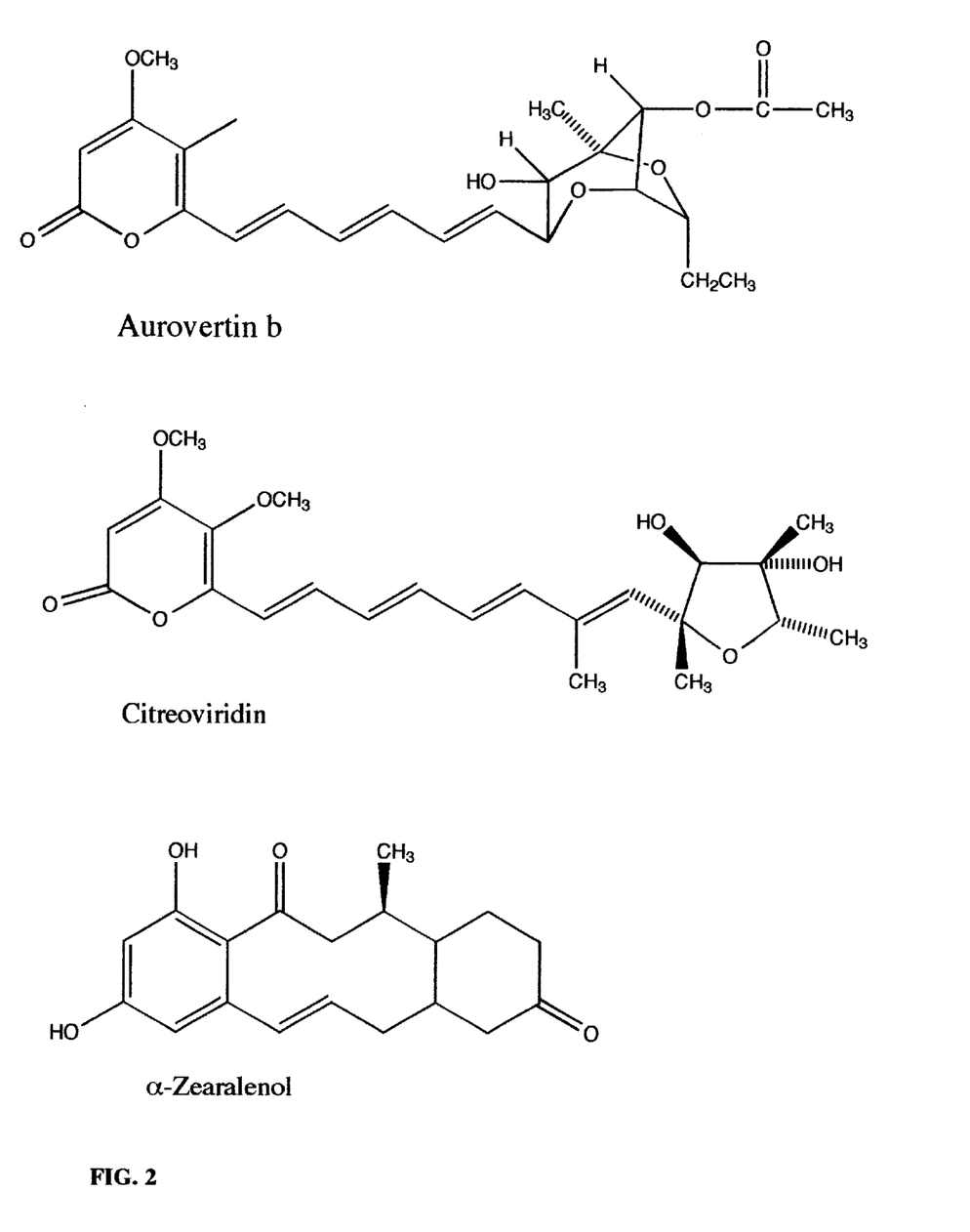
FIG. 2 is a schematic diagram showing the chemicals structures of aurovertin B, citreoviridin, and α-zearalenol.
Figure 3:
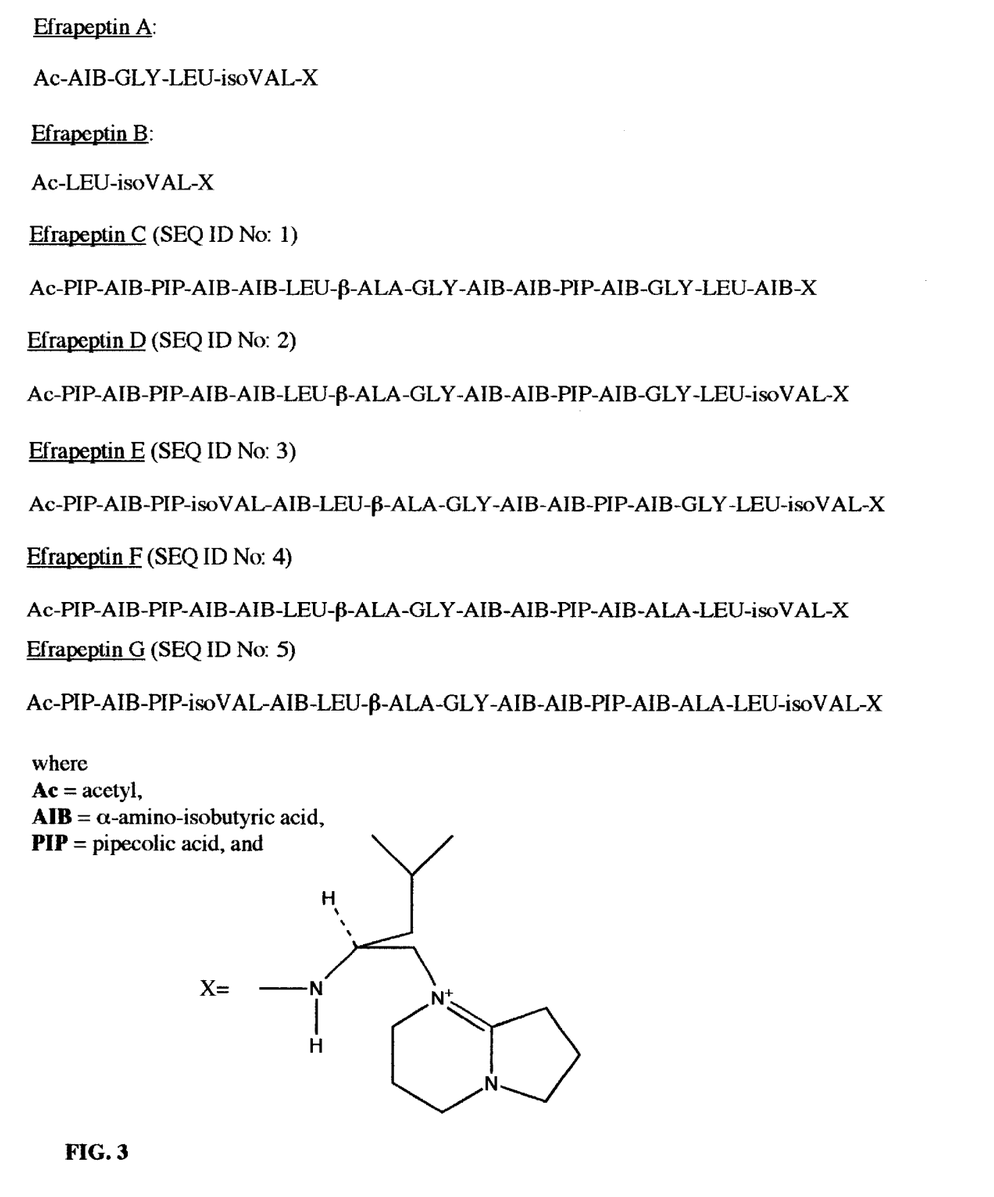
FIG. 3 is a schematic diagram showing the sequence and structure of efrapeptins.
Figure 4A:
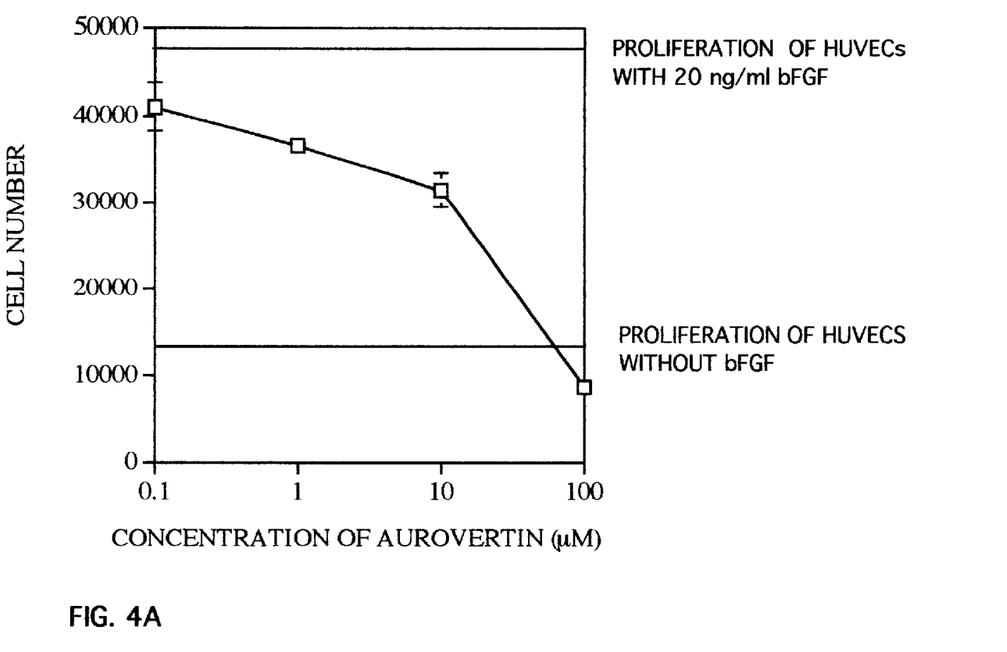
Figure 4B:
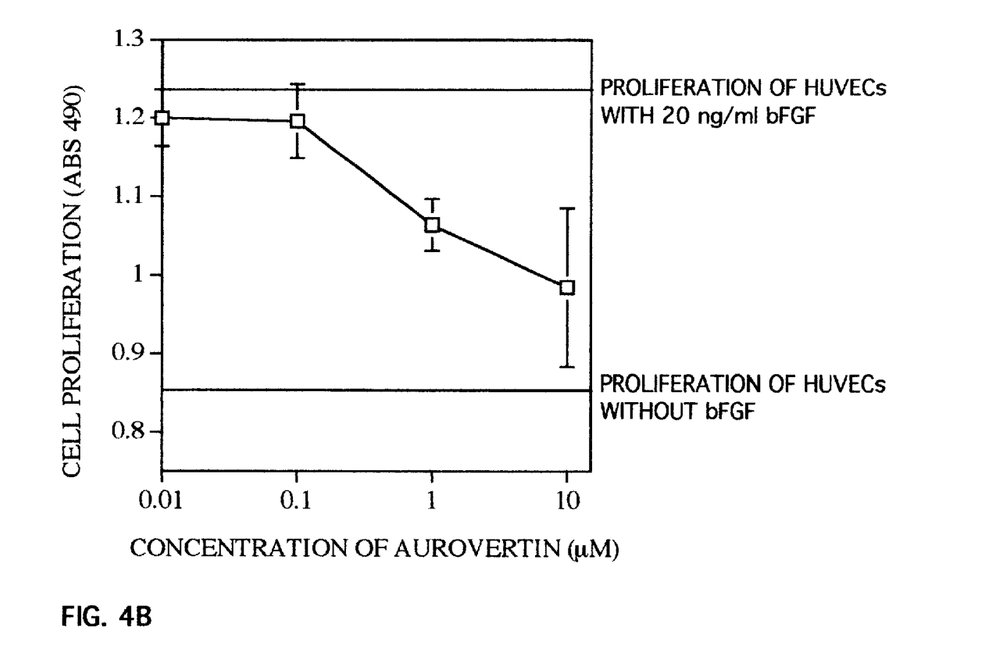
Figure 5:
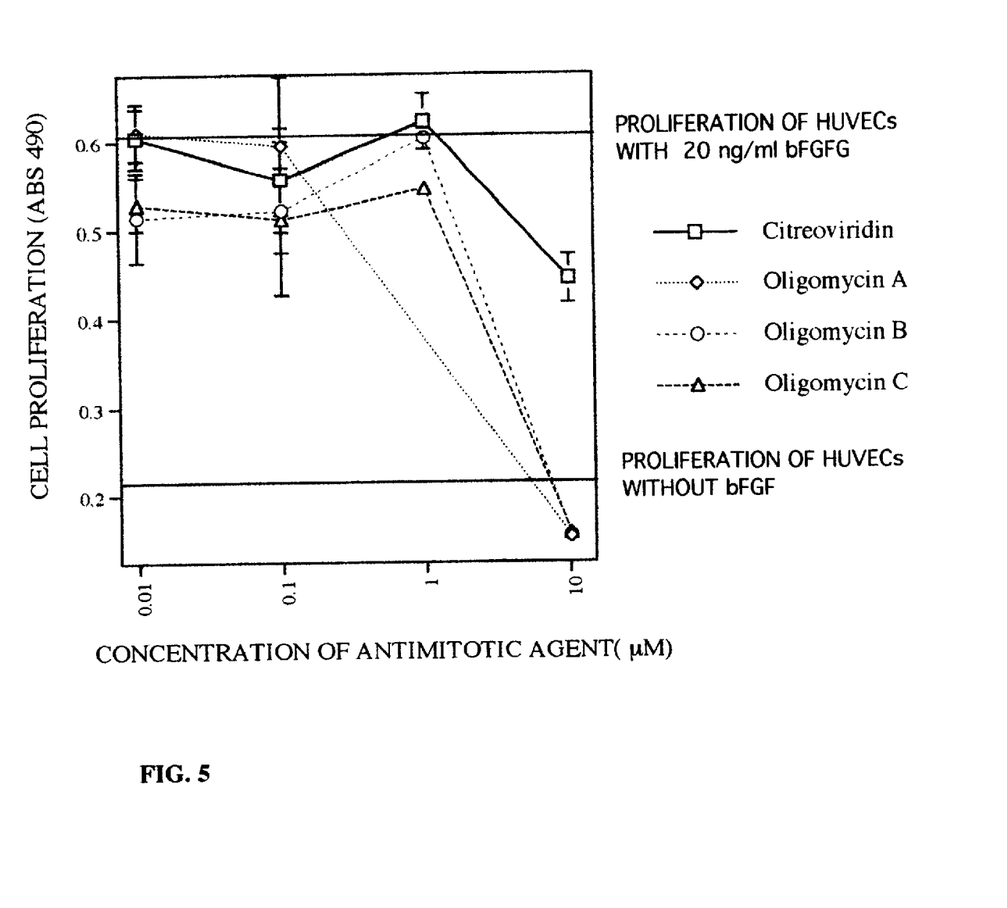
FIG. 5 is a graph depicting the ability of citreoviridin (opened squares), oligomycin A (opened diamonds), oligomycin B (opened circles), and oligomycin C (opened triangles) to inhibit bFGF-induced proliferation of endothelial cells.
Figure 6:
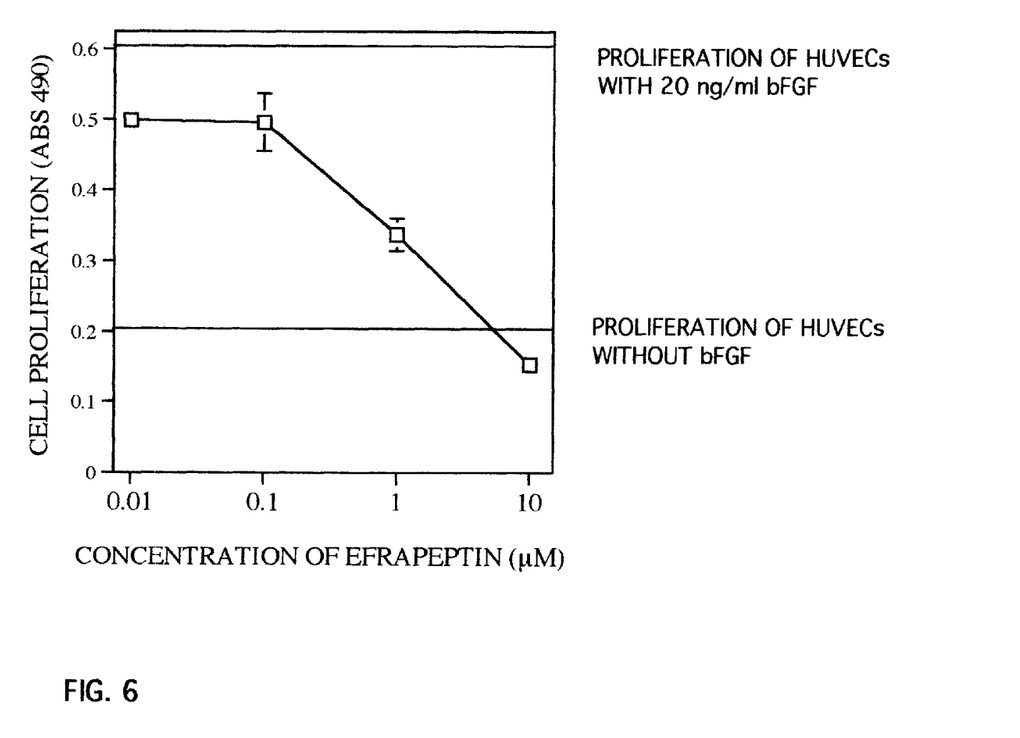
FIG. 6 is a graph depicting the ability of efrapeptin D to inhibit bFGF-induced proliferation of endothelial cells.

All antibiotics tested here inhibited bFGF-induced HUVEC proliferation. The relative antiproliferative effects of aurovertin, citreoviridin, oligomycin A, oligomycin B, oligomycin C, and efrapeptin D are shown graphically in FIGS. 4–6. The $IC_{50}$ of the antiproliferative effects of aurovertin, citreoviridin, oligomycin A, oligomycin B, oligomycin C, and efrapeptin D are reported below:

| Antibiotic | $IC_{50}$ of Antiproliferative Effect |
|---|---|
| Aurovertin | 10 µM |
| Citreoviridin | 10 µM |
| Efrapeptin | 0.5 µM |
| Oligomycin A | 5 µM |
| Oligomycin B | 5 µM |
| Oligomycin C | 5 µM |

EXAMPLE 2

Effect of Aurovertin B on the Vascular Endothelial Growth Factor (VEGF)-induced Migration of Human Endothelial Cells A migration assay familiar to those skilled in the art using vascular endothelial growth factor (VEGF)-stimulated HUVECs was employed to determine the effect of aurovertin B on endothelial cell migration.

Matelials and Methods

The endothelial cells were routinely cultured as previously described.

Modified Boyden chambers in a 48-well format consisting of upper and lower wells separated by an 8-microns pore polycarbonate filter coated with collagen were used to study VEGF-induced migration of HUVECs (Paragon Bioservices, Baltimore, Md.). The endothelial cells were added to the lower wells and the migrating factor (5 ng/ml VEGF) was added to the upper wells. HUVECs were allowed to migrate from the lower to the upper wells for six hours at 37° C., 5% $CO_2$. At the end of the incubation period, the filters were removed and washed gently. The cells on the filters were then fixed, stained with hematoxylin, and counted with a light microscope. The values obtained represent the mean of ten fields.

Results

Figure 7:
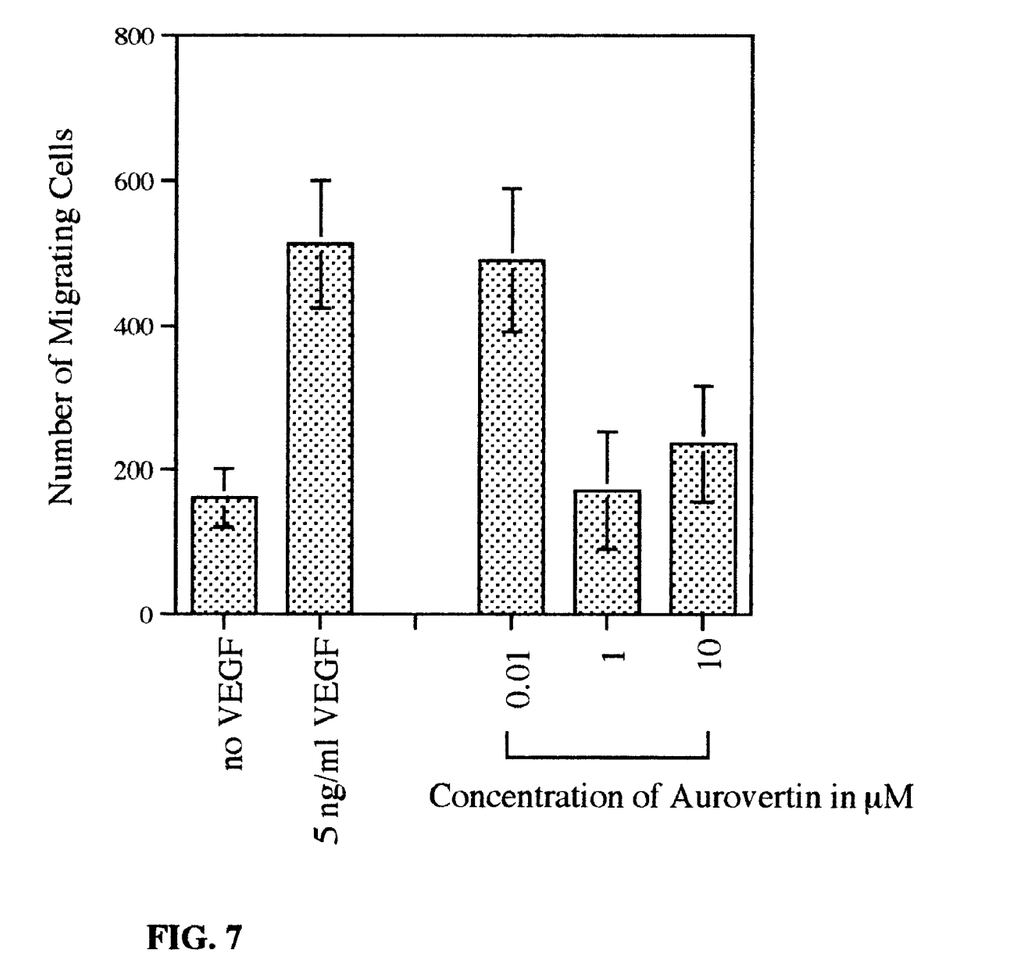
FIG. 7 is a graph depicting the ability of aurovertin B to inhibit VEGF-induced migration of endothelial cells.

Aurovertin B inhibited VEGF-induced migration of HUVECs. The relative antimigratory effect of aurovertin is depicted in FIG. 7.

EXAMPLE 3

Antitumor Effect of Aurovertin B and Efrapeptin D

Materials and Methods

The effect of aurovertin B and efrapeptin D on the growth of murine B16F10 melanoma tumors (ATCC, Rockville, Md.) was investigated. Groups of four C57 mice (The Jackson Laboratory, BarHarbor, Me.) were injected subcutaneously with $5\times10^4$ B16F10 cells (The Jackson Laboratory, BarHarbor, Me.). The mice were subsequently treated i.p. with 2 mg/kg aurovertin B, 0.4 mg/kg efrapeptin D, or vehicle control. The treatment was initiated three days after the tumor inoculation and continued every day for 9 days. The tumor growth was recorded at the end of the experiment.

Results

At the end of the experiment, mice treated with 0.4 mg/kg efrapeptin did not exhibit measurable tumors. Autopsy revealed no pulmonary metastatic lesions. Incision at the tumor site revealed microscopic tumors that had failed to develop. On the contrary, 50% (2/4) of the mice treated with 2 mg/kg aurovertin and 100% (4/4) of the mice treated with vehicle control exhibited measurable, growing tumors at the end of the treatment. The results are summarized in the table below:

| Treatment | Number of mice that developed measurable tumors/ Number of mice injected with tumor cells |
| --- | --- |
| Vehicle Control | 4/4 |
| Aurovertin (2 mg/kg) | 2/4 |
| Efrapeptin (0.4 mg/kg) | 0/4 |

The magnitude of the antitumor effect of efrapeptin and aurovertin is in agreement with the magnitude of the antiangiogenic effect of these antibiotics as determined in the HUVEC proliferation assay.

I claim:

1. A method of inhibiting endothelial cell proliferation in a human or animal comprising administering to the human or animal a therapeutically active dosage of a composition comprising an efrapeptin oligopeptide in a pharmaceutically acceptable carrier.

2. The method of claim 1 wherein the endothelial cell proliferation occurs during angiogenesis-related disease.

3. The method of claim 2 wherein the angiogenesis-related disease is a disease selected from the group consisting of cancer, endometriosis, Kaposis's sarcoma, arthritis, atherosclerosis, psoriasis, macular degeneration, and diabetic retinopathy.

4. A method of inhibiting endothelial cell proliferation occurring during an angiogenesis-related disease in a human or animal comprising administering to the human or animal a therapeutically active dosage of a composition comprising of aurovertin B, citreoviridin, or α-zearalenol in a pharmaceutically acceptable carrier.

5. The method of claim 4 wherein the angiogenesis-related disease is a disease selected from the group consisting of cancer, endometriosis, Kaposis's sarcoma, arthritis, atherosclerosis, psoriasis, macular degeneration, and diabetic retinopathy.

* * * * *

SEQUENCE LISTING

```
<160> NUMBER OF SEQ ID NOS: 5

<210> SEQ ID NO 1
<211> LENGTH: 15
<212> TYPE: PRT
<213> ORGANISM: Tolypocladium niveum
<220> FEATURE:
<221> NAME/KEY: MISC_FEATURE
<222> LOCATION: (1)..(1)
<223> OTHER INFORMATION: ACETYLATION, pipecolic acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (3)..(3)
<223> OTHER INFORMATION: pipecolic acid
<220> FEATURE:
<221> NAME/KEY: MOD_RES
<222> LOCATION: (4)..(5)
<223> OTHER INFORMATION: Aib
<220> FEATURE:
<221> NAME/KEY: MOD_RES
<222> LOCATION: (7)..(7)
<223> OTHER INFORMATION: bAla
<220> FEATURE:
<221> NAME/KEY: MOD_RES
<222> LOCATION: (9)..(10)
<223> OTHER INFORMATION: Aib
<220> FEATURE:
<221> NAME/KEY: MISC_FEATURE
<222> LOCATION: (11)..(11)
<223> OTHER INFORMATION: pipecolic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: BLOCKED, Aib

<400> SEQUENCE: 1
```

```
Xaa Ala Xaa Ala Ala Leu Ala Gly Ala Ala Xaa Ala Gly Leu Ala
1               5                   10                  15
```

<210> SEQ ID NO 2
<211> LENGTH: 15
<212> TYPE: PRT
<213> ORGANISM: Tolypocladium niveum
<220> FEATURE:
<221> NAME/KEY: MISC_FEATURE
<222> LOCATION: (1)..(1)
<223> OTHER INFORMATION: ACETYLATION, pipecolic acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (3)..(3)
<223> OTHER INFORMATION: pipecolic acid
<220> FEATURE:
<221> NAME/KEY: MOD_RES
<222> LOCATION: (4)..(5)
<223> OTHER INFORMATION: Aib
<220> FEATURE:
<221> NAME/KEY: MOD_RES
<222> LOCATION: (7)..(7)
<223> OTHER INFORMATION: bAla
<220> FEATURE:
<221> NAME/KEY: MOD_RES
<222> LOCATION: (9)..(10)
<223> OTHER INFORMATION: Aib
<220> FEATURE:
<221> NAME/KEY: MISC_FEATURE
<222> LOCATION: (11)..(11)
<223> OTHER INFORMATION: pipecolic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: BLOCKED, isovaline

<400> SEQUENCE: 2

```
Xaa Ala Xaa Ala Ala Leu Ala Gly Ala Ala Xaa Ala Gly Leu Val
1               5                   10                  15
```

<210> SEQ ID NO 3
<211> LENGTH: 15
<212> TYPE: PRT
<213> ORGANISM: Tolypolcadium niveum
<220> FEATURE:
<221> NAME/KEY: MISC_FEATURE
<222> LOCATION: (1)..(1)
<223> OTHER INFORMATION: Acetylation, pipecolic acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (3)..(3)
<223> OTHER INFORMATION: pipecolic acic
<220> FEATURE:
<221> NAME/KEY: MOD_RES
<222> LOCATION: (4)..(4)
<223> OTHER INFORMATION: isovaline
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (7)..(7)
<223> OTHER INFORMATION: bAla

```
<220> FEATURE:
<221> NAME/KEY: MOD_RES
<222> LOCATION: (9)..(10)
<223> OTHER INFORMATION: Aib
<220> FEATURE:
<221> NAME/KEY: MISC_FEATURE
<222> LOCATION: (11)..(11)
<223> OTHER INFORMATION: pipecolic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: BLOCKED, isovaline

<400> SEQUENCE: 3

Xaa Ala Xaa Val Ala Leu Ala Gly Ala Ala Xaa Ala Gly Leu Val
1               5                   10                  15

<210> SEQ ID NO 4
<211> LENGTH: 15
<212> TYPE: PRT
<213> ORGANISM: Tolypocladium niveum
<220> FEATURE:
<221> NAME/KEY: MISC_FEATURE
<222> LOCATION: (1)..(1)
<223> OTHER INFORMATION: ACETYLATION, pipecolic acid
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (3)..(3)
<223> OTHER INFORMATION: pipecolic acid
<220> FEATURE:
<221> NAME/KEY: MOD_RES
<222> LOCATION: (4)..(5)
<223> OTHER INFORMATION: Aib
<220> FEATURE:
<221> NAME/KEY: MOD_RES
<222> LOCATION: (7)..(7)
<223> OTHER INFORMATION: bAla
<220> FEATURE:
<221> NAME/KEY: MOD_RES
<222> LOCATION: (9)..(10)
<223> OTHER INFORMATION: Aib
<220> FEATURE:
<221> NAME/KEY: MISC_FEATURE
<222> LOCATION: (11)..(11)
<223> OTHER INFORMATION: pipecolic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: BLOCKED, isovaline

<400> SEQUENCE: 4

Xaa Ala Xaa Ala Ala Leu Ala Gly Ala Ala Xaa Ala Ala Leu Val
1               5                   10                  15

<210> SEQ ID NO 5
<211> LENGTH: 15
<212> TYPE: PRT
<213> ORGANISM: Tolupocladium niveum
<220> FEATURE:
<221> NAME/KEY: MISC_FEATURE
<222> LOCATION: (1)..(1)
<223> OTHER INFORMATION: ACETYLATION, pipecolic acid
<220> FEATURE:
```

-continued

```
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (3)..(3)
<223> OTHER INFORMATION: pipecolic acid
<220> FEATURE:
<221> NAME/KEY: MOD_RES
<222> LOCATION: (4)..(4)
<223> OTHER INFORMATION: isovaline
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (7)..(7)
<223> OTHER INFORMATION: bAla
<220> FEATURE:
<221> NAME/KEY: MOD_RES
<222> LOCATION: (9)..(10)
<223> OTHER INFORMATION: Aib
<220> FEATURE:
<221> NAME/KEY: MISC_FEATURE
<222> LOCATION: (11)..(11)
<223> OTHER INFORMATION: pipecolic acid
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: BLOCKED, isovaline

<400> SEQUENCE: 5

Xaa Ala Xaa Val Ala Leu Ala Gly Ala Ala Xaa Ala Ala Leu Val
1               5                   10                  15
```